United States Patent
Nishimoto et al.

(10) Patent No.: US 8,617,550 B2
(45) Date of Patent: Dec. 31, 2013

(54) TREATMENT OF VASCULITIS WITH IL-6 ANTAGONIST

(75) Inventors: Norihiro Nishimoto, Minoh (JP); Tadamitsu Kishimoto, Tondabayashi (JP); Hideko Nakahara, Osaka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 268 days.

(21) Appl. No.: 10/596,429

(22) PCT Filed: Dec. 17, 2004

(86) PCT No.: PCT/JP2004/019463
§ 371 (c)(1),
(2), (4) Date: Aug. 7, 2006

(87) PCT Pub. No.: WO2005/061000
PCT Pub. Date: Jul. 7, 2005

(65) Prior Publication Data
US 2007/0098714 A1 May 3, 2007

(30) Foreign Application Priority Data
Dec. 19, 2003 (JP) ................................. 2003-423517

(51) Int. Cl.
*A61K 39/395* (2006.01)

(52) U.S. Cl.
USPC .................. 424/139.1; 424/130.1; 424/141.1; 424/142.1; 424/143.1

(58) Field of Classification Search
None
See application file for complete search history.

(56) References Cited

U.S. PATENT DOCUMENTS

| | | | |
|---|---|---|---|
| 5,670,373 A | 9/1997 | Kishimoto | |
| 5,817,790 A | 10/1998 | Tsuchiya et al. | |
| 5,843,994 A * | 12/1998 | Samid | 514/510 |
| 5,851,793 A | 12/1998 | Kishimoto | |
| 5,888,510 A * | 3/1999 | Kishimoto et al. | 424/141.1 |
| 6,428,979 B1 | 8/2002 | Kishimoto | |
| 6,723,319 B1 | 4/2004 | Ito et al. | |
| 7,320,792 B2 * | 1/2008 | Ito et al. | 424/141.1 |
| 7,585,491 B2 * | 9/2009 | Govindan | 424/1.49 |
| 7,612,182 B2 * | 11/2009 | Giles-Komar et al. | 530/388.1 |
| 8,425,912 B2 * | 4/2013 | Govindan | 424/181.1 |
| 2002/0187150 A1 | 12/2002 | Mihara et al. | |
| 2004/0115197 A1 | 6/2004 | Yoshizaki et al. | |
| 2005/0158317 A1 | 7/2005 | Blay et al. | |
| 2006/0251653 A1 * | 11/2006 | Okuda et al. | 424/144.1 |
| 2006/0292147 A1 | 12/2006 | Yoshizaki et al. | |

FOREIGN PATENT DOCUMENTS

| | | |
|---|---|---|
| EP | 0 628 639 A1 | 12/1994 |
| EP | 0 791 359 A1 | 8/1997 |
| EP | 0 983 767 A1 | 3/2000 |
| JP | 08-311098 A | 11/1996 |
| JP | 10324639 A | 12/1998 |
| JP | 2003026699 A | 1/2003 |
| WO | WO 92/19759 A1 | 11/1992 |
| WO | WO 03/048205 A2 | 6/2003 |
| WO | WO 2004/039826 A1 | 5/2004 |
| WO | WO 2004/096273 A1 | 11/2004 |

OTHER PUBLICATIONS

Hirohata et al., Clinical Immunology and Immunopathology 66:225, 1993.*
Noris et al, (Circulation 100:55-60, 1999).*
Hiroshi Hashimoto, "Surveillance Study on Intractable Angitis Comprehensive Research Report in a Financial Year", Heisei 13, Mar. 2002, pp. 47-55, full text with translation.
Shunsei Hirohata et al., "Elevation of Cerebrospinal Fluid Interleukin-6 Activity in Patients with Vasculitides and Central Nervous System Involvement", Clinical Immunology and Immunopathology, vol. 66, No. 3, March, pp. 225-229, 1993.
Marina Noris et al., "Interleukin-6 and Rantes in Takayasu Arteritis", Circulation, Jul. 6, 1999, pp. 55-60.
Norihiro Nishimoto, "Approach for Therapy in the Near Future—Focusing around the Anti-Cytokine Therapy", medicina, vol. 38, No. 3, Mar. 2001, pp. 441-445, full text with translation.
Ryuji Koike, "Systemic erythematosus (SLE) and antiphospholipid antibody syndrome", medicina, vol. 35, No. 10, Oct. 1998, pp. 1728-1730, full text with translation.
International Search Report.
Office Action in counterpart Chilean application 3225-2004, dated Mar. 10, 2009, 9 pages.
Bellomo, R., "Tye Cytokine Network in the Critically Ill," Anaesthesia and Intensive Care, Aug. 1992, 20(3):288-302.
Murata et al., "Development mechanism and pathophysiology," The Saishin-Igaku, Special Issue: A new point of view in pancreatic diseases, Nov. 1992, 47(11):49-56, with English translation, 17 pages.
Ulich et al., "Intratracheal Injection of Endotoxin and Cytokines," American Journal of Pathology, May 1991, 138(5):1097-1101.
Office Action dated Jan. 13, 2011, in corresponding Mexican application No. PA/a/2006/005875, 2 pages.
Katsume et al., "Anti-Interleukin 6 (IL-6) Receptor Antibody Suppresses Castleman's Disease Like Symptoms Emerged in IL-6 Transgenic Mice," Cytokine, Dec. 21, 2002, 20(6):304-311.

(Continued)

*Primary Examiner* — Marianne P Allen
(74) *Attorney, Agent, or Firm* — Foley & Lardner LLP (57) ABSTRACT

To provide a preventive and/or therapeutic agent for vasculitis such as polyarteritis nodosa, the aortitis syndrome, and a vasculitis that is associated with immunological abnormalities, said agent comprising an interleukin-6 (IL-6) antagonist as an active ingredient.

11 Claims, 6 Drawing Sheets

(56) References Cited

OTHER PUBLICATIONS

Tsunenari et al., "Therapeutic Potential of Humanized Anti-interleukin-6 Receptor Antibody: Antitumor Activity in Xenograft Model of Multliple Myeloma," Anticancer Research, 1996, 16:2537-2544.
Nishimoto et al., "Anti-interleukin 6 receotpr antibody treatment in rheumatic disease," Ann. Rheum. Dis., 2000, 59(Suppl 1):i21-i27.
Mihara et al., "IL-6 receptor blockage inhibits the onset of autoimmune kidney disease in NZB/W $F_1$ mice," Clin. Exp. Immunol., 1998, 112:397-402.
Hirata et al., "Humanized anti-interleukin-6 receptor monoclonal antibody induced apoptosis of fresh and cloned human myeloma cells in vitro," Leukemia Research, Apr. 2003, 27(4):343-349.
Supplementary European Search Report dated Jun. 15, 2009 in corresponding EP 04807817.2, 5 pages.
Adachi et al., "The Blockade of IL-6 Signaling in Rational Drug Design," Current Pharmaceutical Design, 2008, 14(12):1217-1224.
Emilie et al., "Production of Interleukin 6 by Granulomas of Giant Cell Arteritis," Human Immunology, 1994, 39(1):17-24.
Kaplanski et al., "IL-6 and IL-8 Production from Cultured Human Endothelial Cells Stimulated by Infection with *Rickettsia conorii* via a Cell-associated IL-$1_\alpha$-dependent Pathway," Journal of Clinical Investigation, 1995, 96(6):2839-2844.
Nishimoto et al., "Successful Treatment of a Patient with Takayasu Arteritis Using a Humanized Anti-Interleukin-6 Receptor Antibody," Arthritis & Rheumatism, Apr. 2008, 58(4):1197-1200.
Norioka et al., "Pretreatment of human vascular smooth muscle cells with interleukin-1 enhances interleukin-6 production and cell proliferation (action of IL-1 on vascular smooth muscle cells," Autoimmunity, 1990, 7(1):41-50.
Stone, John H., "Targeted therapies in systemic vasculitis," Cleveland Clinic Journal of Medicine, Apr. 2002, 69(Supp II):124-128.
Nishimoto et al., "Improvement in Castleman's disease by humanized anti-interleukin-6 receptor antibody therapy," Blood, Jan. 1, 2000, 95(1):56-61.
Guillevin et al., "Vasculitis: mechanisms involved and clinical manifestations," Arthritis Res. Ther., 2007 (published online Aug. 15, 2007), 9(Suppl2):1-9.
Hernandez-Rodriguez et al., "A Strong Initial Systemic Inflammatory Response is Associated with Higher Corticosteroid Requirements and Longer Duration of Therapy in Patients with Giant-Cell Arteritis," Arthritis & Rheumatism, Feb. 2002, 47(1):29-35.
Kuryliszyn-Moskal, A., "Cytokines and Soluble CD4 and CD8 Molecules in Rheumatoid Arthritis: Relationship to Systemic Vasculitis and Microvascular Capillaroscopic Abnormalities," Clin. Rheumatol., 1998, 17:489-495.
Weyand et al., "Treatment of Giant Cell Arteritis," Arthritis & Rheumatism, May 2000, 43(5):1041-1048.
Yoshizaki et al., "Therapy of rheumatoid arthritis by blocking IL-6 signal transduction with a humanized anti-IL-6 receptor antibody," Springer Semin Immunopathol., 1998, 20(1-2):247-259.
"Vasculitis: A Family of Autoimmune Diseases," http://www.aarda.orq/infocus_article.php?ID=30, 2004-2012, retrieved Dec. 14, 2012.

\* cited by examiner

Fig. 6

TREATMENT OF VASCULITIS WITH IL-6 ANTAGONIST

TECHNICAL FIELD

The present invention relates to a novel preventive and/or therapeutic agent for vasculitis.

BACKGROUND ART

Vasculitis is one of the intractable pathological conditions commonly observed in autoimmune diseases, and many cases thereof are refractory to conventionally-used therapeutic methods such as steroids and immunosuppressants and, therefore, new therapeutic methods have been sought. In the vasculitis syndrome, inflammation occurs in arteries of various sizes, and fever, pain in muscles and joints, vascular occlusion, skin ulcer, and mononeuritis multiplex may develop. Vasculitis includes intractable vasculitis syndromes such as polyarteritis nodosa and the aortitis syndrome. Lesions of polyarteritis nodosa are characterized by necrotic inflammations of the media and the adventitia, and aortitis usually develops inflammations of the intima, the media and the adventitia.

Aortitis is also called Takayasu's arteritis. The pathology of vasculitis has been suggested to be associated with IL-6. For example, Noris et al. have reported that blood levels of IL-6 are increased in patients with Takayasu's arteritis in the active stage of pathology compared to normal healthy people (Circulation 1999 Jul. 6; 100 (1); 55-60). However, this paper also reports that the serum concentration of RANTES, one of the kemokines, is also enhanced. Noris et al. also suggest the possibility that these cytokines are responsible for vasculitic lesions in patients with Takayasu's arteritis.

DISCLOSURE OF THE INVENTION

The paper, however, does not make any mention of the possibility that Takayasu's arteritis can be treated by inhibiting IL-6. Thus, the present invention provides a preventive and/or therapeutic agents for vasculitis comprising an IL-6 antagonist as an active ingredient.

After intensive and extensive research, the present inventors have demonstrated that IL-6 is indispensable in the pathology of vasculitis and that an IL-6 antagonist has a therapeutic effect for vasculitis. More surprisingly, in the study by the present inventors, when the binding of IL-6 to its receptor was inhibited by an IL-6 receptor antibody IL-6 per se was decreased in the blood. Thus, it was demonstrated that the IL-6 inhibition therapy not only has an anti-inflammatory effect on vasculitis per se but also treats vasculitis per se by acting on the core of vasculitis.

Thus, the present invention provides a preventive and/or therapeutic agent for vasculitis, said agent comprising an interleukin-6 (IL-6) antagonist as an active ingredient.

The present invention provides a preventive and/or therapeutic agent for vasculitis having resistance to steroids and/or immunosuppressants, said agent comprising an interleukin-6 (IL-6) antagonist as an active ingredient.

Said vasculitis is for example polyarteritis nodosa, the aortitis syndrome, or a vasculitis that is associated with immunological abnormalities. The aortitis syndrome is also termed as Takayasu's arteritis. As vasculitis associated with immunological abnormalities, for example, there can be mentioned vasculitis associated with rheumatoid and vasculitis associated with systemic lupus erythematosus (SLE).

Said IL-6 antagonist is, for example, an antibody against IL-6 or an antibody against IL-6 receptor, preferably a monoclonal antibody against IL-6 receptor. Said antibody against IL-6 receptor is most preferably a monoclonal antibody against human IL-6 receptor, for example PM-1 antibody, or a monoclonal antibody against mouse IL-6 receptor, for example MR16-1 antibody. Said antibody against IL-6 receptor is preferably a recombinant antibody.

Said antibody against IL-6 receptor can be a chimeric antibody, humanized antibody, or human antibody. As used herein the most preferably antibody is a humanized PM-1 antibody.

The present invention can also have the following aspects:

(1) The use of interleukin-6 (IL-6) antagonist for the manufacture of a preventive and/or therapeutic agent for vasculitis.

(2) The use of interleukin-6 (IL-6) antagonist for the manufacture of a preventive and/or therapeutic agent for vasculitis having resistance to steroids and/or immunosuppressants.

(3) The use according to the above (1) or (2) wherein said vasculitis is polyarteritis nodosa.

(4) The use according to the above (1) or (2) wherein said vasculitis is the aortitis syndrome.

(5) The use according to the above (1) or (2) wherein said vasculitis is vasculitis associated with immunological abnormalities.

(6) The use according to any of the above (1) to (5) wherein said IL-6 antagonist is an antibody against IL-6 receptor.

(7) The use according to the above (6) wherein said antibody against IL-6 receptor is a monoclonal antibody against IL-6 receptor.

(8) The use according to the above (6) wherein said antibody against IL-6 receptor is a monoclonal antibody against human IL-6 receptor.

(9) The use according to the above (6) wherein said antibody against IL-6 receptor is a monoclonal antibody against mouse IL-6 receptor.

(10) The use according to any of the above (6) to (9) wherein said antibody against IL-6 receptor is a recombinant antibody.

(11) The use according to the above (8) wherein said monoclonal antibody against human IL-6 receptor is PM-1 antibody.

(12) The use according to the above (9) wherein said monoclonal antibody against mouse IL-6 receptor is MR16-1 antibody.

(13) The use according to any of the above (6) to (12) wherein said antibody against IL-6 receptor is a chimeric antibody, a humanized antibody, or a human antibody.

(14) The use according to the above (13) wherein said humanized antibody against IL-6 receptor is a humanized PM-1 antibody.

(15) A method of preventing and/or treating vasculitis comprising administering an interleukin-6 (IL-6) antagonist.

(16) A method of preventing and/or treating vasculitis having resistance to steroids and/or immunosuppressants comprising administering an interleukin-6 (IL-6) antagonist.

(17) The method according to the above (15) or (16) wherein said vasculitis is polyarteritis nodosa.

(18) The method according to the above (15) or (16) wherein said vasculitis is the aortitis syndrome.

(19) The method according to the above (15) or (16) wherein said vasculitis is vasculitis associated with immunological abnormalities.

(20) The method according to any of the above (15) to (19) wherein said IL-6 antagonist is an antibody against IL-6 receptor.

(21) The method according to the above (20) wherein said antibody against IL-6 receptor is a monoclonal antibody against IL-6 receptor.

(22) The method according to the above (20) wherein said antibody against IL-6 receptor is a monoclonal antibody against human IL-6 receptor.

(23) The method according to the above (20) wherein said antibody against IL-6 receptor is a monoclonal antibody against mouse IL-6 receptor.

(24) The method according to any of the above (20) to (23) wherein said antibody against IL-6 receptor is a recombinant antibody.

(25) The method according to the above (22) wherein said monoclonal antibody against human IL-6 receptor is PM-1 antibody.

(26) The method according to the above (23) wherein said monoclonal antibody against mouse IL-6 receptor is MR1 antibody.

(27) The method according to any of the above (20) to (26) wherein said antibody against IL-6 receptor is a chimeric antibody, humanized antibody, or a human antibody against IL-6 receptor.

(28) The method according to the above (27) wherein said humanized antibody against IL-6 receptor is a humanized PM-1 antibody.

BEST MODE FOR CARRYING OUT THE INVENTION

IL-6 is a cytokine which is also called B cell stimulating factor 2 (BSF2) or interleukin β2. IL-6 was discovered as a differentiation factor involved in the activation of B-lymphatic cells (Hirano, T. et al., Nature (1986) 324, 73-76). Thereafter, it was found to be a multifunctional cytokine that influences various functions of cells (Akira, S. et al., Adv. in Immunology (1993) 54, 1-78). IL-6 has been reported to induce the maturation of T-lymphatic cells (Lotz, M. et al., J. Exp. Med. (1988) 167, 1253-1258).

IL-6 transmits its biological activity through two types of proteins on the cell. One of them is IL-6 receptor, a ligand-biding protein with a molecular weight of about 80 kD, to which IL-6 binds (Taga, T. et al., J. Exp. Med. (1987) 166, 967-9381; Yamasaki, K. et al., Science (1987) 241, 825-828). IL-6 receptor occurs not only in the membrane-bound form that penetrates through and is expressed on the cell membrane but also as a soluble IL-6 receptor consisting mainly of the extracellular region.

The other is a membrane-bound protein gp130 having a molecular weight of about 130 kD that is involved in non-ligand-binding signal transduction. IL-6 and IL-6 receptor form the IL-6/IL-6 receptor complex which, after binding to gp130, transmits its biological activity to the cell (Taga, T. et al., Cell (1989) 58, 573-581).

An IL-6 antagonist is a substance that inhibits the transduction of biological activity of IL-6. As the IL-6 antagonist, there have been known so far antibody directed against IL-6 (anti-IL-6 antibody), antibody directed against IL-6 receptor (anti-IL-6 receptor antibody), and antibody directed against gp130 (anti-gp130 antibody), altered IL-6, partial peptides of IL-6 or IL-6 receptor and the like.

Anti-IL-6 receptor antibody has been described in several reports (Novick D. et al., Hybridoma (1991) 10, 137-146, Huang, Y. W. et al., Hybridoma (1993) 12, 621-630, International Patent Publication WO 95-09873, French Patent Application FR 2694767, U.S. Pat. No. 521,628). A humanized PM-1 antibody has been known that was obtained by transplanting the complementarity determining region (CDR) of one of them, a mouse antibody PM-1 (Hirata, Y. et al., J. Immunology (1989) 143, 2900-2906), to a human antibody (the International Patent Publication WO 92-19759).

The above IL-6 antagonist is preferably an antibody against IL-6 receptor, preferably a monoclonal antibody against human IL-6 receptor or a monoclonal antibody against mouse IL-6 receptor. As the above monoclonal antibody against human IL-6 receptor, there can be illustrated PM-1 antibody, and as the above monoclonal antibody against mouse IL-6 receptor, there can be illustrated MR16-1 antibody. The above antibody is preferably a chimeric antibody, humanized antibody or a human antibody, for example a humanized PM-1 antibody.

IL-6 antagonists for use in the present invention may be of any origin, any kind, and any form, as long as they are useful as an active ingredient for a preventive or therapeutic effect for vasculitis.

IL-6 antagonists block signal transduction by IL-6 and inhibit the biological activity of IL-6. IL-6 antagonists are preferably substances that have an activity of inhibiting any of IL-6, IL-6 receptor, and gp130. As the IL-6 antagonists, there can be mentioned, for example, anti-IL-6 antibody, anti-IL-6 receptor antibody, anti-gp130 antibody, altered IL-6, altered soluble IL-6 receptor, a partial peptide of IL-6 or IL-6 receptor, and a low molecular weight substances having the same activity as these.

Anti-IL-6 antibodies for use in the present invention can be obtained as polyclonal or monoclonal antibodies using a known method. As the anti-IL-6 antibodies for use in the present invention, monoclonal antibodies of, in particular, a mammalian origin, are preferred. Monoclonal antibodies of a mammalian origin include those produced by a hybridoma and recombinant antibody produced by a host which has been transformed with an expression vector containing genetically engineered antibody genes. These antibodies, via binding to IL-6, block the binding of IL-6 to IL-6 receptor, and thereby blocks signal transduction of the biological activity of IL-6 into the cell.

Examples of such antibodies include MH166 (Matsuda et al., Eur. J. Immunol. (1988) 18, 951-956) and SK2 antibody (Sato, K. et al., The 21st Nihon Menekigakkai Soukai (General Meeting of the Japan Immunology Society), Academic Record (1991) 21, 166) and the like.

An anti-IL-6 antibody-producing hybridoma can be basically constructed using a known procedure as described below. Thus, IL-6 may be used as a sensitizing antigen and is immunized in the conventional method of immunization. The immune cells thus obtained are fused with known parent cells in the conventional cell fusion process, and then monoclonal antibody-producing cells are screened by the conventional screening method to prepare the desired hybridoma.

Specifically, anti-IL-6 antibody may be obtained in the following manner. For example, a human IL-6 for use as the sensitizing antigen to obtain antibody can be obtained using the IL-6 gene/amino acid sequence disclosed in Eur. J. Biochem (1987) 168, 543-550, J. Immunol. (1988) 140, 1534-1541, or Argic. Biol. (1990) 54, 2685-2688.

After a suitable host cell is transformed by inserting the IL-6 gene sequence into a known expression vector system, the IL-6 protein of interest is purified from the host cell or the culture supernatant thereof, and the purified IL-6 protein can be used as the sensitizing antigen. Alternatively, a fusion protein of the IL-6 protein and another protein may be used as the sensitizing antigen.

Anti-IL-6 receptor antibodies for use in the present invention can be obtained as polyclonal or monoclonal antibodies using a known method. As the anti-IL-6 antibodies for use in the present invention, monoclonal antibodies of, in particular, a mammalian origin, are preferred. Monoclonal antibodies of a mammalian origin include those produced by a hybridoma and those produced by a host which has been transformed with an expression vector containing genetically engineered antibody genes. The antibodies, via binding to IL-6 receptor, inhibit the binding of IL-6 to IL-6 receptor, and thereby block the transduction of the biological activity of IL-6 into the cell.

Examples of such antibodies include MR16-1 antibody (Tamura, T., et al., Proc. Natl. Acad. Sci. USA (1993) 90, 11924-11928), PM-1 antibody (Hirata, et al., J. Immunol. (1989) 143, 2900-2906), or AUK12-20 antibody, AUK64-7 antibody or AUK146-15 antibody (International Patent Publication WO 92-19759), and the like. Among them, PM-1 antibody is most preferred.

Incidentally, the hybridoma cell line which produces PM-1 antibody has been internationally deposited under the provisions of the Budapest Treaty as PM-1 on Jul. 12, 1995 with the Patent Microorganism Depository of the National Institute of Industrial Science and Technology, at Chuo 6, 1-1, Higashi 1-chome, Tsukuba city, Ibaraki pref., Japan, as FERM BP-2998. The hybridoma cell line which produces MR16-1 antibody has been internationally deposited under the provisions of the Budapest Treaty as MR16-1 on Mar. 13, 1997 with the Patent Microorganism Depository of the National Institute of Industrial Science and Technology, at Chuo 6, 1-1, Higashi 1-chome, Tsukuba city, Ibaraki pref., Japan, as FERM BP-5875.

Hybridomas producing anti-IL-6 receptor monoclonal antibody can be basically prepared using a known procedure as described below. Thus, IL-6 receptor is used as a sensitizing antigen and is immunized according to the conventional method of immunization. The immune cells thus obtained are fused with known parent cells in the conventional cell fusion process, and then monoclonal antibody-producing cells may be screened by the conventional screening method to prepare the desired hybridoma.

Specifically, anti-IL-6 receptor antibody may be prepared in the following manner. For example, the human IL-6 receptor used as the sensitizing antigen for obtaining antibody can be obtained using the IL-6 receptor gene sequence/amino acid sequence disclosed in European Patent Application EP 325474, and the mouse IL-6 receptor can be obtained using the IL-6 receptor gene disclosed in Japanese Unexamined Patent Publication (Kokai) 3-155795.

There are two types of IL-6 receptor proteins: IL-6 receptor expressed on the cell membrane, and IL-6 receptor detached from the cell membrane (soluble IL-6 Receptor) (Yasukawa et al., J. Biochem. (1990) 108, 673-676). Soluble IL-6 receptor antibody is composed substantially of the extracellular region of the IL-6 receptor bound to the cell membrane and, thereby, is different from the membrane-bound IL-6 receptor in that the former lacks the transmembrane region or both of the transmembrane region and the intracellular region. As the IL-6 receptor protein, any IL-6 receptor can be used, as long as it can be used a sensitizing antigen for production of the IL-6 receptor antibody for use in the present invention.

After the gene sequence of IL-6 receptor is inserted into a known expression vector system to transform an appropriate host cell, the desired IL-6 receptor protein may be purified from the host cell or a culture supernatant thereof using a known method, and the purified IL-6 receptor protein thus purified may be used as the sensitizing antigen. Alternatively, cells that are expressing IL-6 receptor or a fusion protein of the IL-6 receptor protein and another protein may be used as the sensitizing antigen.

*E. coli* that has a plasmid pIBIBSF2R containing cDNA encoding human IL-6 receptor has been internationally deposited under the provisions of the Budapest Treaty as HB101-pIBIBSF2R on Jan. 9, 1989 with the Patent Microorganism Depository of the National Institute of Industrial Science and Technology, at Chuo 6, 1-1, Higashi 1-chome, Tsukuba city, Ibaraki pref., Japan, as FERM BP-2232.

Anti-gp130 antibodies for use in the present invention can be obtained as polyclonal or monoclonal antibodies using a known method. As the anti-gp130 antibodies for use in the present invention, monoclonal antibodies of, in particular, a mammalian origin, are preferred. Monoclonal antibodies of a mammalian origin include those produced by a hybridoma and those produced by a host which has been transformed with an expression vector containing genetically engineered antibody genes. The antibodies, via binding to gp130, inhibit the binding of IL-6/IL-6 receptor complex to gp130, and thereby block the transduction of the biological activity of IL-6 into the cell.

Examples of such antibodies include AM64 antibody (Japanese Unexamined Patent Publication (Kokai) 3-219894), 4B11 antibody and 2H4 antibody (U.S. Pat. No. 5,571,513), B-S12 antibody and B-P8 antibody (Japanese Unexamined Patent Publication (Kokai) 8-291199).

An anti-gp130 monoclonal antibody-producing hybridoma can be basically created using a known procedure as described below. Thus, gp130 may be used as a sensitizing antigen and is immunized in the conventional method of immunization. The immune cells thus obtained are fused with known parent cells in the conventional cell fusion process and, then, the monoclonal antibody-producing hybridomas are screened by the conventional screening method to prepare the desired hybridoma.

Specifically, monoclonal antibody may be obtained in the following manner. For example, gp130 used as the sensitizing antigen for antibody generation can be obtained using the gp130 gene sequence/amino acid sequence disclosed in European Patent Application EP 411946.

After a suitable host cell is transformed by inserting the gp130 gene sequence into a known expression vector system, the gp130 protein of interest is purified from the host cell or from the culture supernatant thereof. The purified gp130 receptor protein can be used as the sensitizing antigen. Alternatively, a fusion protein of the gp130 protein and another protein may be used as the sensitizing antigen.

Though mammals to be immunized with the sensitizing antigen are not specifically limited, they are preferably selected in consideration of their compatibility with the parent cell for use in cell fusion. They generally include rodents such as mice, rats, hamsters and the like.

Immunization of animals with a sensitizing antigen is carried out using a known method. A general method, for example, involves the intraperitoneal or subcutaneous administration of a sensitizing antigen to the mammal. Specifically, a sensitizing antigen which has been diluted and suspended in an appropriate amount of phosphate buffered saline (PBS) or physiological saline etc. is mixed, as desired, with an appropriate amount of a common adjuvant, for example Freund's complete adjuvant. After being emulsified, it is preferably administered to a mammal for several times every 4 to 21 days. Alternatively a suitable carrier may be used at the time of immunization of the sensitizing antigen.

After immunization and the confirmation of the increase in the desired antibody levels in the serum, the immune cells are taken out from the mammal and are subjected to cell fusion. Preferred immune cells to be subjected to cell fusion include, in particular, the spleen cells.

The mammalian myeloma cells as the other parent cells which are fused with the above-mentioned immune cells preferably include various known cell lines such as P3X63Ag8.653 (Kearney, J. F. et al., C. Immunol. (1979) 123; 1548-1550), P3X63Ag8U.1 (Current Topics in Microbiology and Immunology (1978) 81; 1-7), NS-1 (Kohler, G. and Milstein, C., Eur. J. Immunol. (1976) 6; 511-519), MPC-11 (Margulies, D. H. et al., Cell (1976) 8; 405-415), SP2/0 (Shulman, M. et al., Nature (1978) 276; 269-270), FO (de St. Groth, S. F. et al., J. Immunol. Methods (1980) 35; 1-21), S194 (Trowbridge, I. S., J. Exp. Med. (1978) 148; 313-323), R210 (Galfre, G. et al., Nature (1979) 277; 131-133) and the like.

Cell fusion between the above immune cells and the myeloma cells may be essentially conducted in accordance with a known method such as is described in Milstein et al. (Kohler, G. and Milstein, C., Methods Enzymol. (1981) 73; 3-46) and the like.

More specifically, the above cell fusion is carried out in a conventional nutrient broth in the presence of, for example, a cell fusion accelerator. As the cell fusion accelerator, for example, polyethylene glycol (PEG), Sendai virus (HVJ) and the like may be used, and, in addition, an adjuvant such as dimethyl sulfoxide etc. may be added as desired to enhance the efficiency of fusion.

The preferred ratio of the immune cells and the myeloma cells to be used is, for example, 1 to 10 times more immune cells than the myeloma cells. Examples of culture media to be used for the above cell fusion include RPMI1640 medium and MEM culture medium suitable for the growth of the above myeloma cell lines, and the conventional culture medium used for this type of cell culture, and besides a serum supplement such as fetal calf serum (FCS) may be added.

In cell fusion, predetermined amounts of the above immune cells and the myeloma cells are mixed well in the above culture liquid, to which a PEG solution previously heated to about 37° C., for example a PEG solution with a mean molecular weight of about 1000 to 6000, is added at a concentration of 30 to 60% (w/v) and mixed to obtain the desired fusion cells (hybridoma). Then by repeating the sequential addition of a suitable culture liquid and centrifugation to remove the supernatant, cell fusion agents etc. which are undesirable for the growth of the hybridoma can be removed.

Said hybridoma is selected by culturing in the conventional selection medium, for example, the HAT culture medium (a culture liquid containing hypoxanthine, aminopterin, and thymidine). Culturing in said HAT culture medium is continued generally for a period of time sufficient to effect killing of the cells other than the desired hybridoma (non-fusion cells), generally several days to several weeks. The conventional limiting dilution method is conducted in which the hybridomas that produce the desired antibody are screened and monclonally cloned.

In addition to obtaining the above hybridoma by immunizing an animal other than a human with an antigen, it is also possible to sensitize human lymphocytes in vitro with a desired antigen or desired antigen-expressing cells, and the resulting sensitized B lymphocytes are fused with human myeloma cells, for example U266, to obtain the desired human antibody having the activity of binding to the desired antigen or the desired antigen-expressing cells (see Japanese Post-examined Patent Publication (Kokoku) No. 1-59878). Furthermore, a transgenic animal having a repertoire of all human antibody genes can be immunized with the antigen or the antigen-expressing cells to obtain the desired human antibody in the method described above (see International Patent Publication WO 93/12227, WO 92/03918, WO 94/02602, WO 94/25585, WO 96/34096 and WO 96/33735).

The monoclonal antibody-producing hybridoma thus constructed can be subcultured in the conventional culture liquid, or can be stored for a prolonged period of time in liquid nitrogen.

In order to obtain monoclonal antibodies from said hybridoma, a method can be used in which said hybridoma is cultured in the conventional method and the antibodies are obtained as the supernatant, or a method in which the hybridoma is administered to, and grown in, a mammal compatible with said hybridoma and the antibodies are obtained as the ascites. The former method is suitable for obtaining high-purity antibodies, whereas the latter is suitable for a large scale production of antibodies.

For example, a hybridoma producing anti-IL-6 receptor antibody can be constructed using the method disclosed in Japanese Unexamined Patent Publication (Kokai) 3-139293. It can be conducted by a method in which the PM-1 antibody-producing hybridoma that was internationally deposited under the provisions of the Budapest Treaty as FERM BP-2998 on Jul. 12, 1989 with the Patent Microorganism Depository of the National Institute of Industrial Science and Technology, at Chuo 6, 1-1, Higashi 1-chome, Tsukuba city, Ibaraki pref., Japan, is intraperitoneally injected to BALB/c mice to obtain the ascites from which the PM-1 antibody is purified, or a method in which said hybridoma is cultured in a suitable culture medium such as the RPMI1640 medium containing 10% bovine fetal serum and 5% MB-Condimed H1 (manufactured by Boehringer Mannheim), the hybridoma SFM medium (manufactured by GIBCO-BRL), the PFHM-II medium (manufactured by GIBCO-BRL) and the like, and the PM-1 antibody can be purified from the supernatant.

A recombinant antibody which was produced by the recombinant gene technology in which an antibody gene was cloned from the hybridoma and integrated into a suitable vector which was then introduced into a host can be used in the present invention as monoclonal antibody (see, for example, Borrebaeck C. A. K., and Larrick J. W. THERA- PEUTIC MONOCLONAL ANTIBODIES, published in the United Kingdom by MACMILLAN PUBLISHERS LTD. 1990).

Specifically, mRNA encoding the variable (V) region of the desired antibody is isolated from antibody-producing cells such as a hybridoma. The isolation of mRNA is conducted by preparing total RNA using, for example, a known method such as the guanidine ultracentrifuge method (Chirgwin, J. M. et al., Biochemistry (1979) 18, 5294-5299), the AGPC method (Chomczynski, P. et al., Anal. Biochem. (1987) 162, 156-159), and then mRNA is purified from the total RNA using the mRNA Purification kit (manufactured by Pharmacia) and the like. Alternatively, mRNA can be directly prepared using the Quick Prep mRNA Purification Kit (manufactured by Pharmacia).

cDNA of the V region of antibody may be synthesized from the mRNA thus obtained using a reverse transcriptase. cDNA may be synthesized using the AMV Reverse Transcriptase First-strand cDNA Synthesis Kit and the like. Alternatively, for the synthesis and amplification of cDNA, the 5'-Ampli FINDER RACE Kit (manufactured by Clontech) and the 5'-RACE method (Frohman, M. A. et al., Proc. Natl. Acad. Sci. USA (1988) 85, 8998-9002; Belyavsky, A. et al., Nucleic Acids Res. (1989) 17, 2919-2932) that employs polymerase chain reaction (PCR) may be used. The desired DNA fragment is purified from the PCR product obtained and may be ligated to vector DNA. Moreover, a recombinant vector is constructed therefrom and then is introduced into *E. coli* etc., from which colonies are selected to prepare the desired recombinant vector. The base sequence of the desired DNA may be confirmed by a known method such as the dideoxy method.

Once the DNA encoding the V region of the desired antibody has been obtained, it may be ligated to DNA encoding the constant region (C region) of the desired antibody, which is then integrated into an expression vector. Alternatively, the DNA encoding the V region of the antibody may be integrated into an expression vector containing DNA encoding the C region of the antibody.

In order to produce the antibody for use in the present invention, the antibody gene is integrated as described below into an expression vector so as to be expressed under the control of the expression regulatory region, for example an enhancer and/or a promoter. Subsequently, the expression vector may be transformed into a host cell and the antibody can then be expressed therein.

In accordance with the present invention, an artificially altered recombinant antibody such as chimeric antibody, humanized antibody, and human antibody can be used for the purpose of lowering heterologous antigenicity against humans. These altered antibodies can be produced using known methods.

Chimeric antibody can be obtained by ligating the thus obtained DNA encoding the V region of antibody to DNA encoding the C region of human antibody, which is then integrated into an expression vector and introduced into a host for production of the antibody therein (see European Patent Application EP 125023, and International Patent Publication WO 92-19759). Using this known method, chimeric antibody useful for the present invention can be obtained.

For example, a plasmid that contains DNA encoding the L chain V region or the H chain V region of chimeric PM-1 antibody was designated as pPM-k3 or pPM-h1, respectively, and *E. coli* having the plasmid has been internationally deposited under the provisions of the Budapest Treaty as NCIMB 40366 and NCIMB 40362, respectively, on Feb. 12, 1991 with the National Collections of Industrial and Marine Bacteria Limited (23 St Machar Drive, Aberdeen, Scotland, AB2 1RY, United Kingdom of Great Britain and Northern Ireland).

Humanized antibody, which is also called reshaped human antibody, has been made by transplanting the complementarity determining region (CDR) of antibody of a mammal other than a human, for example mouse antibody, into the CDR of human antibody. The general recombinant DNA technology for preparation of such antibodies is also known (see European Patent Application EP 125023 and International Patent Publication WO 92-19759).

Specifically, a DNA sequence which was designed to ligate the CDR of mouse antibody with the framework region (FR) of human antibody is synthesized from several divided oligonucleotides having sections overlapping with one another at the ends thereof. The DNA thus obtained is ligated to the DNA encoding the C region of human antibody and then is integrated into an expression vector, which is introduced into a host for antibody production (see European Patent Application EP 239400 and International Patent Publication WO 92-19759).

For the FR of human antibody ligated through CDR, the complementarity determining region that forms a favorable antigen binding site is selected. When desired, amino acids in the framework region of the antibody variable region may be substituted so that the complementarity determining region of reshaped human antibody may form an appropriate antigen biding site (Sato, K. et al., Cancer Res. (1993) 53, 851-856).

For example, for chimeric antibody or humanized antibody, the C region of human antibody is used. As the C region of human antibody, there can be mentioned C$\gamma$, and C$\gamma$1, C$\gamma$2, C$\gamma$3, and C$\gamma$4, for example, can be used. The C region of human antibody may be modified to improve the stability of antibody or the production thereof.

Chimeric antibody consists of the variable region of antibody derived from a mammal other than the human and the C region derived from human antibody, whereas humanized antibody consists of the complementarity determining region of antibody derived from a mammal other than the human and the framework region and the C region of antibody derived from human antibody. Accordingly, antigenicity thereof in the human body has been reduced so that they are useful as an antibody for use in the present invention.

As a preferred embodiment of the humanized antibody for use in the present invention, there can be mentioned humanized PM-1 antibody (see International Patent Publication WO 92-19759).

Furthermore, as a method of obtaining human antibody, a technology that employs panning with a human antibody library is known, in addition to those described above. For example, the variable region of human antibody is expressed on the surface of a phage by the phage display method as a single chain antibody (scFv) to select a phage that binds to the antigen. By analyzing the gene of the phage selected, the DNA sequence encoding the variable region of the human antibody that binds to the antigen can be determined. Once the DNA sequence of scFv that binds to the antigen is clarified, it is possible to construct an appropriate expression vector that contains said sequence and then to obtain a human antibody. These methods are already known and can be found in WO 92/01047, WO 92/20791, WO 93/06213, WO 93/11236, WO 93/19172, WO 95/01438, and WO 95/15388.

Antibody genes constructed as described above may be expressed and obtained in a known method. In the case of mammalian cells, expression may be accomplished using a vector containing a commonly used useful promoter, the antibody gene to be expressed, DNA in which the poly A signal has been operably linked at 3' downstream thereof or a vector containing said DNA. Examples of the promoter/enhancer include human cytomegalovirus immediate early promoter/enhancer.

Additionally, as the promoter/enhancer which can be used for expression of antibody for use in the present invention, there can be used viral promoters/enhancers such as retrovirus, polyoma virus, adenovirus, and simian virus 40 (SV40), and promoters/enhancers derived from mammalian cells such as human elongation factor 1α(HEF1α).

For example, expression may be readily accomplished by the method of Mulligan et al. (Mulligan, R. C. et al., Nature (1979) 277, 108-114) when SV40 promoter/enhancer is used, or by the method of Mizushima et al. (Mizushima, S. and Nagata, S. Nucleic Acids Res. (1990) 18, 5322) when HEF1α promoter/enhancer is used.

In the case of *E. coli*, expression may be conducted by operably linking a commonly used useful promoter, a signal sequence for antibody secretion, and the antibody gene to be expressed, followed by expression thereof. As the promoter, for example, there can be mentioned lacZ promoter and araB promoter. The method of Ward et al. (Ward, E. S. et al., Nature (1098) 341, 544-546; Ward, E. S. et al., FASEB J. (1992) 6, 2422-2427) may be used when lacz promoter is used, and the method of Better et al. (Better, M. et al., Science (1988) 240, 1041-1043) may be used when araB promoter is used.

As the signal sequence for antibody secretion when produced in the periplasm of *E. coli*, the pelB signal sequence (Lei, S. P. et al., J. Bacteriol. (1987) 169, 4379-4383) can be used. After separating the antibody produced in the periplasm, the structure of the antibody is appropriately refolded before use (see, for example, WO 96/30394).

As the origin of replication, there can be used those derived from SV40, polyoma virus, adenovirus, bovine papilloma virus (BPV) and the like. Furthermore, for the amplification of the gene copy number in the host cell system, expression vectors can include as selectable markers the aminoglycoside phosphotransferase (APH) gene, the thymidine kinase (TK) gene, *E. coli* xanthine guanine phosphoribosyl transferase (Ecogpt) gene, the dihydrofolate reductase (dhfr) gene and the like.

For the production of antibody for use in the present invention, any production system can be used, The production system for antibody preparation comprises the in vitro or the in vivo production system. As the in vitro production system, there can be mentioned a production system which employs eukaryotic cells and the production system which employs prokaryotic cells.

When the eukaryotic cells are used, there are the production systems which employ animal cells, plant cells, or fungal cells. Known animal cells include (1) mammalian cells such as CHO cells, COS cells, myeloma cells, baby hamster kidney (BHK) cells, HeLa cells, and Vero cells, (2) amphibian cells such as *Xenopus oocytes*, or (3) insect cells such as sf9, sf21, and Tn5. Known plant cells include, for example, those derived from *Nicotiana tabacum*, which may be subjected to callus culture. Known fungal cells include yeasts such as the genus Saccharomyces, more specifically *Saccharomyces cereviceae*, or filamentous fungi such as the genus *Aspergillus*, more specifically *Aspergillus niger.*

When the prokaryotic cells are used, there are the production systems which employ bacterial cells, Known bacterial cells include *Escherichia coli* (*E. coli*), and *Bacillus subtilis*.

By introducing, via transformation, the gene of the desired antibody into these cells and culturing the transformed cells in vitro, the antibody can be obtained. Culturing is conducted in the known methods. For example, as the culture liquid, DMEM, MEM, RPMI1640, and IMDM can be used, and serum supplements such as fetal calf serum (FCS) may be used in combination. In addition, antibodies may be produced in vivo by implanting cells into which the antibody gene has been introduced into the abdominal cavity of an animal and the like.

As in vivo production systems, there can be mentioned those which employ animals and those which employ plants. When animals are used, there are the production systems which employ mammals and insects.

As mammals, goats, pigs, sheep, mice, and cattle can be used (Vicki Glaser, SPECTRUM Biotechnology Applications, 1993). Also, as insects, silkworms can be used. When plants are used, tobacco, for example, can be used.

Antibody genes are introduced into these animals or plants, and the antibodies are produced in such animals or plants, and recovered. For example, an antibody gene is inserted into the middle of the gene encoding protein which is inherently produced in the milk such as goat β casein to prepare fusion genes. DNA fragments containing the fusion gene into which the antibody gene has been inserted are injected into a goat embryo, and the embryo is introduced into a female goat. The desired antibody is obtained from the milk produced by the transgenic goat born to the goat who received the embryo or offsprings thereof. In order to increase the amount of milk containing the desired antibody produced by the transgenic goat, hormones may be given to the transgenic goat as appropriate. (Ebert, K. M. et al., Bio/Technology (1994) 12, 699-702).

When silkworms are used, baculovirus into which the desired antibody gene has been inserted is infected to the silkworm, and the desired antibody can be obtained from the body fluid of the silkworm (Maeda, S. et al., Nature (1985) 315, 592-594). Moreover, when tobacco is used, the desired antibody gene is inserted into an expression vector for plants, for example pMON 530, and then the vector is introduced into a bacterium such as *Agrobacterium tumefaciens*. The bacterium is then infected to tobacco such as *Nicotiana tabacum* to obtain the desired antibody from the leaves of the tobacco (Julian, K.-C. Ma et al., Eur. J. Immunol. (1994) 24, 131-138).

When antibody is produced in in vitro or in in vivo production systems, as described above, DNA encoding the heavy chain (H chain) or the light chain (L chain) of antibody may be separately integrated into an expression vector and the hosts are transformed simultaneously, or DNA encoding the H chain and the L chain may be integrated into a single expression vector, and the host is transformed therewith (see International Patent Publication WO 94-11523).

Antibodies for use in the present invention may be antibody fragments or modified versions thereof as long as they are preferably used. For example, as fragments of antibody, there may be mentioned Fab, F(ab')$_2$, Fv or single-chain Fv (scFv) in which Fv's of H chain and L chain were ligated via a suitable linker.

Specifically, antibodies are treated with an enzyme, for example, papain or pepsin, to produce antibody fragments, or genes encoding these antibody fragments are constructed, and then introduced into an expression vector, which is expressed in a suitable host cell (see, for example, Co, M. S. et al., J. Immunol. (1994) 152, 2968-2976; Better, M. and Horwitz, A. H., Methods in Enzymology (1989) 178, 476-496; Plueckthun, A. and Skerra, A., Methods in Enzymology (1989) 178, 476-496; Lamoyi, E., Methods in Enzymology (1989) 121, 652-663; Rousseaux, J. et al., Methods in Enzymology (1989) 121, 663-66; Bird, R. E. et al., TIBTECH (1991) 9, 132-137).

scFv can be obtained by ligating the V region of H chain and the V region of L chain of antibody. In scFv, the V region of H chain and the V region of L chain are preferably ligated via a linker, preferably a peptide linker (Huston, J. S. et al., Proc. Natl. Acad. Sci. USA (1988) 85, 5879-5883). The V region of H chain and the V region of L chain in scFv may be derived from any of the above-mentioned antibodies. As the peptide linker for ligating the V regions, any single-chain peptide comprising, for example, 12-19 amino acid residues may be used.

DNA encoding scFv can be obtained using DNA encoding the H chain or the H chain V region of the above antibody and DNA encoding the L chain or the L chain V region of the above antibody as the template by amplifying the portion of the DNA encoding the desired amino acid sequence among the above sequences by the PCR technique with the primer pair specifying the both ends thereof and by further amplifying the combination of DNA encoding the peptide linker portion and the primer pair which defines that both ends of said DNA be ligated to the H chain and the L chain, respectively.

Once DNAs encoding scFv have been constructed, an expression vector containing them and a host transformed with said expression vector can be obtained by the conventional methods, and scFv can be obtained using the resultant host by the conventional methods.

These antibody fragments can be produced by obtaining the gene thereof in a similar manner to that mentioned above and by allowing it to be expressed in a host. "Antibody" as used herein also encompasses these antibody fragments.

As modified antibodies, antibodies associated with various molecules such as polyethylene glycol (PEG) can be used. "Antibody" as used herein also encompasses these modified antibodies. These modified antibodies can be obtained by chemically modifying the antibodies thus obtained. These methods have already been established in the art.

Antibodies produced and expressed as described above can be separated from the inside or outside of the host cell and then may be purified to homogeneity. Separation and purification of the antibody for use in the present invention may be accomplished by affinity chromatography. As the column used for such affinity chromatography, there can be mentioned Protein A column and Protein G column. Examples of the carriers used in the Protein A column are Hyper D, POROS, Sepharose F. F. and the like. Alternatively, methods for separation and purification conventionally used for proteins can be used without any limitation.

Separation and purification of the antibody for use in the present invention may be accomplished by combining, as appropriate, chromatography other than the above-mentioned affinity chromatography, filtration, ultrafiltration, salting-out, dialysis and the like. Chromatography includes, for example, ion exchange chromatography, hydrophobic chromatography, gel-filtration and the like. These chromatographies can be applied into high performance liquid chromatography (HPLC). Alternatively, reverse-phase HPLC can be used.

The concentration of antibody obtained in the above can be determined by the measurement of absorbance or by the enzyme-linked immunosorbent assay (ELISA) and the like. Thus, when absorbance measurement is employed, a sample is appropriately diluted with PBS(−) and then the absorbance is measured at 280 nm, followed by calculation using the absorption coefficient of 1.35 OD at 1 mg/ml. When the ELISA method is used, measurement is conducted as follows. Thus, 100 µl of goat anti-human IgG (manufactured by TAG) diluted to 1 µg/ml in 0.1 M bicarbonate buffer, pH 9.6, is added to a 96-well plate (manufactured by Nunc), and is incubated overnight at 4° C. to immobilize the antibody. After blocking, 100 µl each of an appropriately diluted antibody of the present invention or a sample containing the antibody, or 100 µl of human IgG (manufactured by CAPPEL) as the standard is added, and incubated at room temperature for 1 hour.

After washing, 100 µl of 5000-fold diluted alkaline phosphatase-labeled anti-human IgG antibody (manufactured by BIO SOURCE) is added, and incubated at room temperature for 1 hour. After washing, the substrate solution is added and incubated, followed by the measurement of absorbance at 405 nm using the MICROPLATE READER Model 3550 (manufactured by Bio-Rad) to calculate the concentration of the desired antibody.

The altered IL-6 for use in the present invention has an activity of binding to IL-6 receptor and does not transmit the biological activity of IL-6. Thus, the altered IL-6, though it competes with IL-6 for binding to IL-6 receptor, does not transmit the biological activity of IL-6, and thereby it blocks signal transduction by IL-6.

Altered IL-6 may be constructed through the introduction of mutation by replacing amino acid residues of the amino acid sequence of IL-6. IL-6, the source of the altered IL-6, may be of any origin, but when the antigenicity is to be considered, it is preferably human IL-6.

Specifically, the secondary structure of IL-6 is predicted using a known molecular modeling program of the amino acid sequencer for example WHATIF (Vriend et al., J. Mol. Graphics (1990), 8, 52-56), and the overall effects on the amino acid residue to be replaced is evaluated. After an appropriate amino acid residue has been determined, mutation is introduced to effect amino acid substitution by the commonly used polymerase chain reaction (PCR) method using a vector containing the base sequence encoding human IL-6 gene as a template thereby to obtain a gene encoding an altered IL-6. This is then integrated, as desired, into an appropriate expression vector, from which the altered IL-6 can be obtained according to the expression, production and purification methods of said recombinant antibody.

Specific examples of the altered IL-6 are disclosed in Brakenhoff et al., J. Biol. Chem. (1994) 269, 86-93, and Savino et al., EMBO J. (1994) 13, 1357-1367, WO 96-18648, and WO 96-17869.

The IL-6 partial peptide or the IL-6 receptor partial peptide for use in the present invention has an activity of binding to IL-6 receptor or IL-6, respectively, and does not transmit the biological activity of IL-6. Thus, the IL-6 partial peptide or the IL-6 receptor partial peptide specifically inhibits the binding of IL-6 to IL-6 receptor by binding to IL-6 receptor or IL-6, respectively, and thereby capturing it. As a result, they do not transmit the biological activity of IL-6, and thus block signal transduction of IL-6.

The IL-6 partial peptide or the IL-6 receptor partial peptide is a peptide comprising some or all of the amino acid sequence of the region involved in the binding to IL-6 and IL-6 receptor in the amino acid sequence of IL-6 or IL-6 receptor. Such a peptide generally comprises 10-80, preferably 20-50, more preferably 20-40 amino acid residues.

The IL-6 partial peptide or the IL-6 receptor partial peptide can be constructed by specifying the region involved in the binding to IL-6 and IL-6 receptor in the amino acid sequence of IL-6 or IL-6 receptor, and by producing some or all of the amino acid sequence by a conventional method such as a genetic engineering technology or a peptide synthesis method.

In order to prepare the IL-6 partial peptide or the IL-6 receptor partial peptide by a genetic engineering technology, the DNA sequence encoding the desired peptide is integrated into an expression vector, from which the peptide can be obtained by the expression, production, and purification methods of said recombinant antibody.

Preparation of the IL-6 partial peptide or the IL-6 receptor partial peptide by the peptide synthesis method can be effected using a method commonly used in peptide synthesis such as the solid phase synthesis or the liquid phase synthesis.

Specifically the method described in Zoku-Iyakuhin no Kaihatsu (Sequel to Development of Pharmaceuticals), Vol. 14, Peputido Gousei (Peptide Synthesis), edited by Haruaki Yajima, Hirokawa Shoten, 1991, may be used. The solid phase synthesis method used includes, for example, a reaction in which an amino acid corresponding to the C-terminal of the peptide to be synthesized is coupled to a support which is insoluble in organic solvents, and then an amino acid in which α-amino group or a side chain functional group has been protected with an appropriate protecting group is condensed one amino acid at a time from the C-terminal to the N-terminal direction, and a reaction in which said protecting group of the α-amino group of the amino acid or the peptide coupled to the resin is eliminated are alternately repeated to elongate the peptide chain. The solid phase peptide synthesis methods are divided into the Boc method and the Fmoc method depending on the type of protecting group to be used.

After the synthesis of the desired peptide is complete, a deprotection reaction and a reaction for cleaving the peptide chain from the support is carried out. For cleavage from the peptide chain, hydrogen fluoride or trifluoromethane sulfonic acid in the Boc method, and TFA in the Fmoc method are generally used. In the Boc method, for example, the above peptide resin is treated in hydrogen fluoride in the presence of anisole. Subsequently, the protecting group is eliminated and the peptide is recovered by cleaving from the support. By lyophilizing this, a crude peptide can be obtained. On the other hand, in the Fmoc method, the deprotection reaction and the cleavage reaction of the peptide from the support may be performed in TFA for example, in a manner procedure similar to the above.

The crude peptide thus obtained can be applied to HPLC for its separation and purification. Its elution can be carried out in a water-acetonitrile solvent system that is commonly used for protein purification under an optimum condition. The fraction corresponding to the peak of the profile of the chromatography obtained is collected and lyophilized. The peptide fraction thus purified is identified by subjecting it to the analysis of molecular weight by mass spectroscopic analysis, the analysis of amino acid composition, or the analysis of amino acid sequence, and the like.

Specific examples of the IL-6 partial peptide or the IL-6 receptor partial peptide are disclosed in Japanese Unexamined Patent Publication (Kokai) 2-188600, Japanese Unexamined Patent Publication (Kokai) 7-324097, Japanese Unexamined Patent Publication (Kokai) 8-311098, and United States Patent Publication U.S. Pat. No. 5,210,075.

The activity of the IL-6 antagonist for use in the present invention of blocking signal transduction of IL-6 can be evaluated using a conventionally known method. Specifically, the IL-6-dependent human myeloma cell line (S6B45, KPMM2), human Lennert's T-lymphoma cell line KT3, or IL-6-dependent cell MH60.BSF2 is cultured, to which IL-6 is added, and the activity can be evaluated using the incorporation of $^3$H-thymidine into the IL-6-dependent cell in the coexistence of the IL-6 antagonist.

Alternatively, U266, a IL-6 receptor-expressing cell, may be culture, to which $^{125}$I-labeled IL-6 is added and an IL-6 antagonist is added at the same time, and then the $^{125}$I-labeled IL-6 bound to the IL-6 receptor-expressing cell is determined.

In the above assay system, a negative control group containing no IL-6 antagonists, in addition to the group in which an IL-6 receptor antagonist is present, is set up, and the results obtained for them are compared to evaluate the IL-6-inhibiting activity of the IL-6 receptor antagonist.

As described in the Example below, anti-IL-6 receptor antibody exhibited a therapeutic effect of vasculitis, suggesting that IL-6 antagonists such as anti-IL-6 receptor antibody are effective as a therapeutic agent for vasculitis.

The subject to be treated in the present invention is mammals. The subject mammal to be treated is preferably humans.

The preventive or therapeutic agents of the present invention may be administered, either orally or parenterally, systemically or locally. For example, intravenous injection such as drip infusion, intramuscular injection, intraperitoneal injection, subcutaneous injection, suppositories, intestinal lavage, oral enteric coated tablets, and the like can be selected, and the method of administration may be chosen, as appropriate, depending on the age and the conditions of the patient. The effective dosage is chosen from the range of 0.01 mg to 100 mg per kg of body weight per administration. Alternatively, the dosage in the range of 1 to 20 mg, preferably 2 to 8 mg per patient may be chosen.

Preferred dosages and preferred methods of administration are such that, in the case of anti-IL-6 receptor antibody, amounts wherein free antibody is present in the blood are effective dosages. In specific examples, 1 mg to 20 mg per kg of body weight, preferably 2 mg to 8 mg, per month (4 weeks) are administered in one to several doses, for example twice per week, once per week, once every two weeks, once every four weeks, and the like by intravenous injection such as drip infusion and subcutaneous injection. The administration schedule can be adjusted by observing the disease conditions and blood levels of laboratory tests by, for example, extending the administration interval from twice per week or once per week to once per two weeks, once per three weeks, once per four weeks, and the like.

The preventive or therapeutic agents for vasculitis of the present invention may contain pharmaceutically acceptable carriers or additives depending on the route of administration. Examples of such carriers or additives include water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof depending on the dosage form.

EXAMPLES

The present invention will now be explained in more details with reference to the working examples and reference examples. It should be noted, however, that the present invention is not limited by them in any way.

Working Example 1

Method:
Patients with intractable vasculitis syndrome (polyarteritis nodosa, the aortitis syndrome) refractory to the conventional therapy were subjected to treatment with humanized anti- IL-6 receptor antibody. Under the permission by the Advanced Medical Treatment Committee of the Osaka University Hospital, two patients received humanized PM-1 antibody (MRA) that is a humanized anti-IL-6 receptor antibody. The end-point was the improvement in evaluation of images by magnetic resonance imaging (MRI) and computerized tomography (CT), improvement in skin conditions, improvement in inflammatory markers such as C reactive protein (CRP), and improvement in QOL (pain, arthralgia, malaise) Also, peripheral blood cell counts, general biochemistry, homostatic function, IL-6, soluble IL-6 receptor, the concentration of humanized anti-IL-6 receptor antibody in the blood, tumor necrosis factor α (TNFα), interleukin-1b (IL-1b), and vascular epidermal growth factor (VEGF) were evaluated.

Result:

Case 1:

A 19-year old female. Diagnosed as having the aortitis syndrome in 1996. Had a complication of ulcerative colitis. Prednisolone (PSL) 60 mg/day was started. Even the combined use of cyclosporin could not reduce PSL to 20 mg/day or lower. In 1998, in response to aggravation, cyclophosphamide 150 mg/day was used in addition to the methyl prednisolone (mPSL) pulse therapy, but could not be reduced to 30 mg/day or lower. Betamethasone 1 mg/day was added, and then leukopheresis was performed for seven times, but without effect. In 2000 and after, the mPSL pulse therapy was intermittently used, and azathioprine 100 mg/day, mycophenolate mofetil 2 g/day, and methotrexate 17.5 mg/week were used in combination, but without effect.

Figure 1:
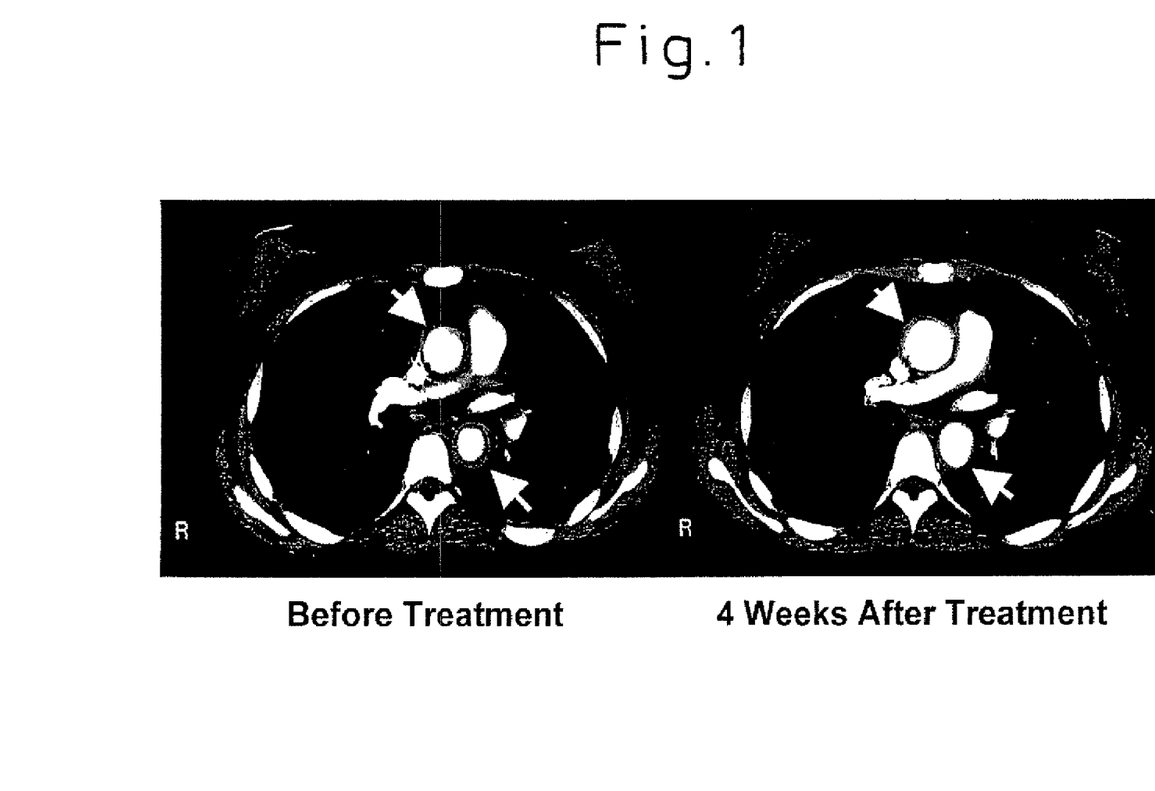
FIG. 1 is a photograph showing the result of CT in the treatment of the vasculitis syndrome with humanized IL-6R antibody, in which the upper arrow indicates the ascending aorta and the lower arrow indicates the descending aorta
Figure 2:
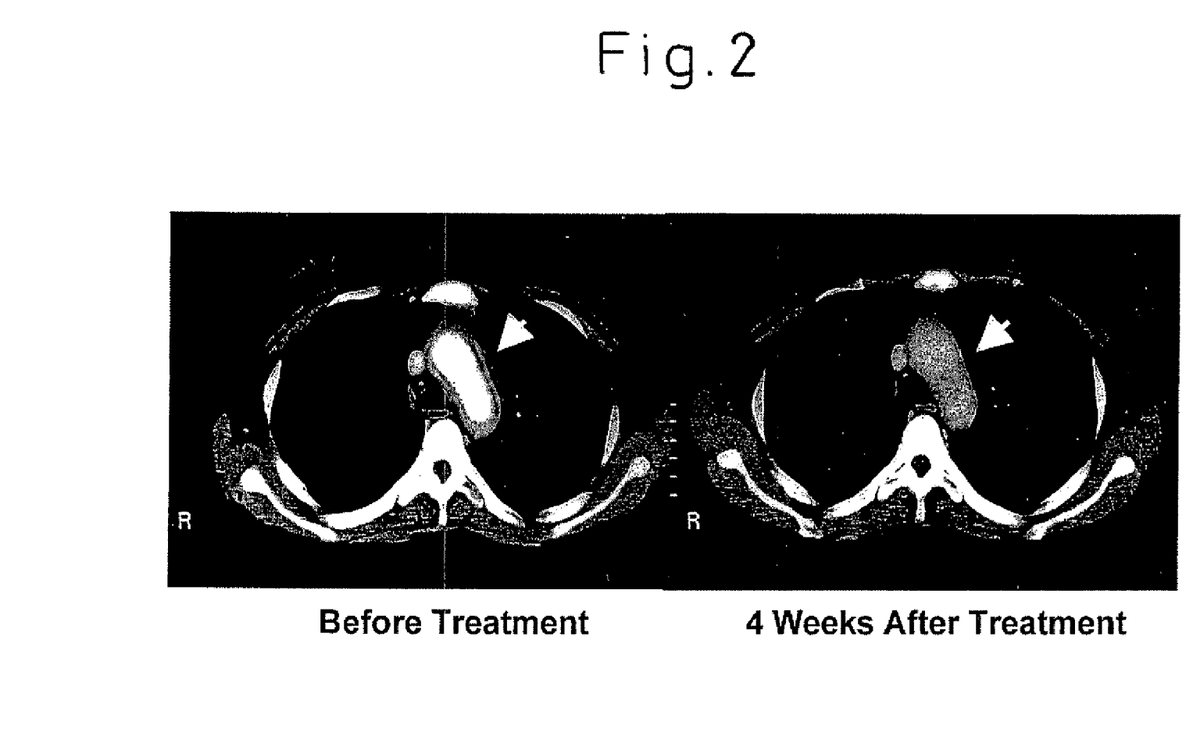
FIG. 2 is a photograph showing the result of CT in the treatment of the vasculitis syndrome with humanized IL-6R antibody, in which the arrow indicates the aortic arch.
Figure 3:
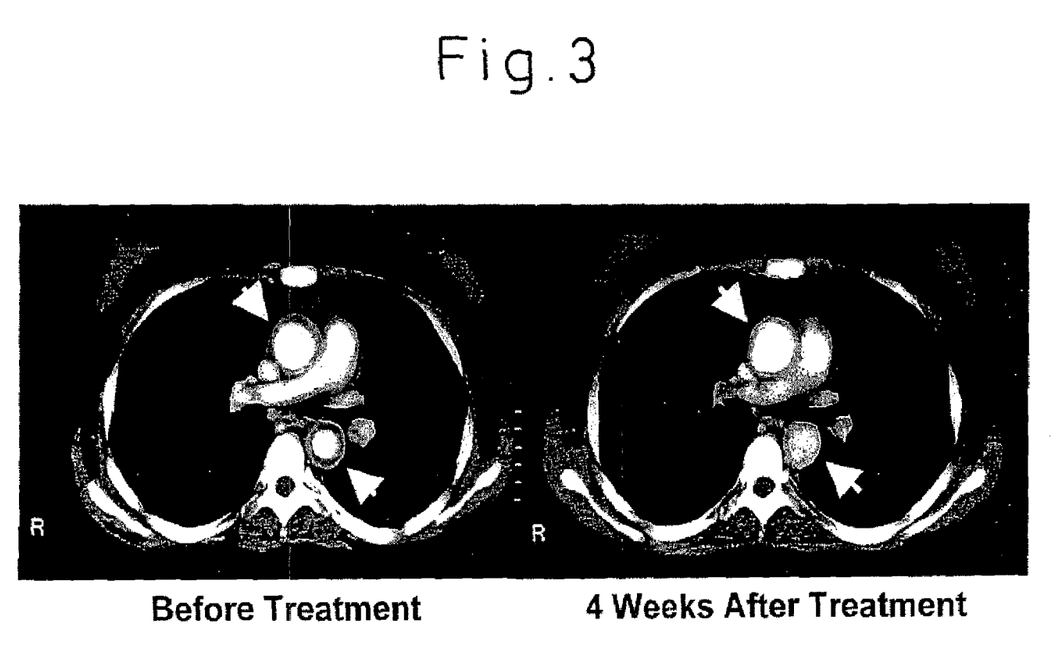
FIG. 3 is a photograph showing the result of CT in the treatment of the vasculitis syndrome with humanized IL-6R antibody, in which the upper arrow indicates the ascending aorta and the lower arrow indicates the descending aorta
Figure 4:
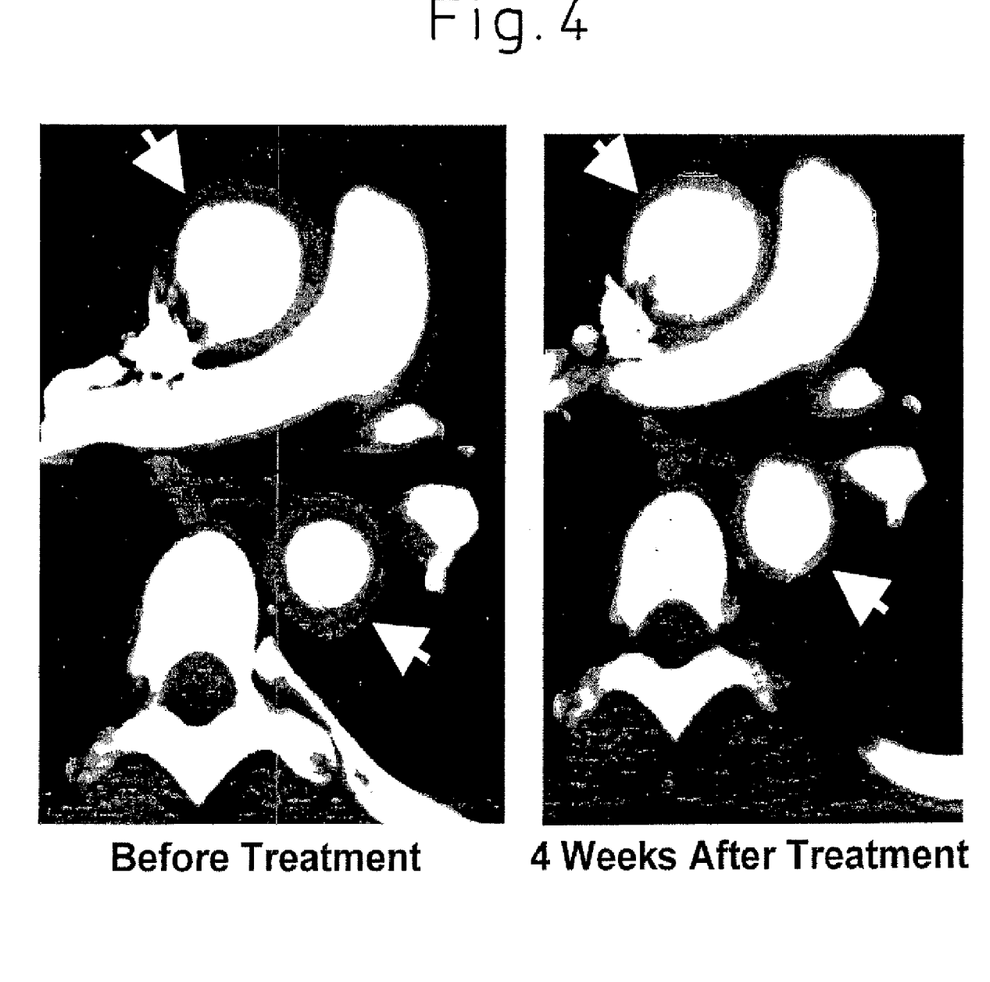
FIG. 4 is a photograph showing the result of CT in the treatment of the vasculitis syndrome with humanized IL-6R antibody, in which the upper arrow indicates the ascending aorta and the lower arrow indicates the descending aorta
Figure 5:
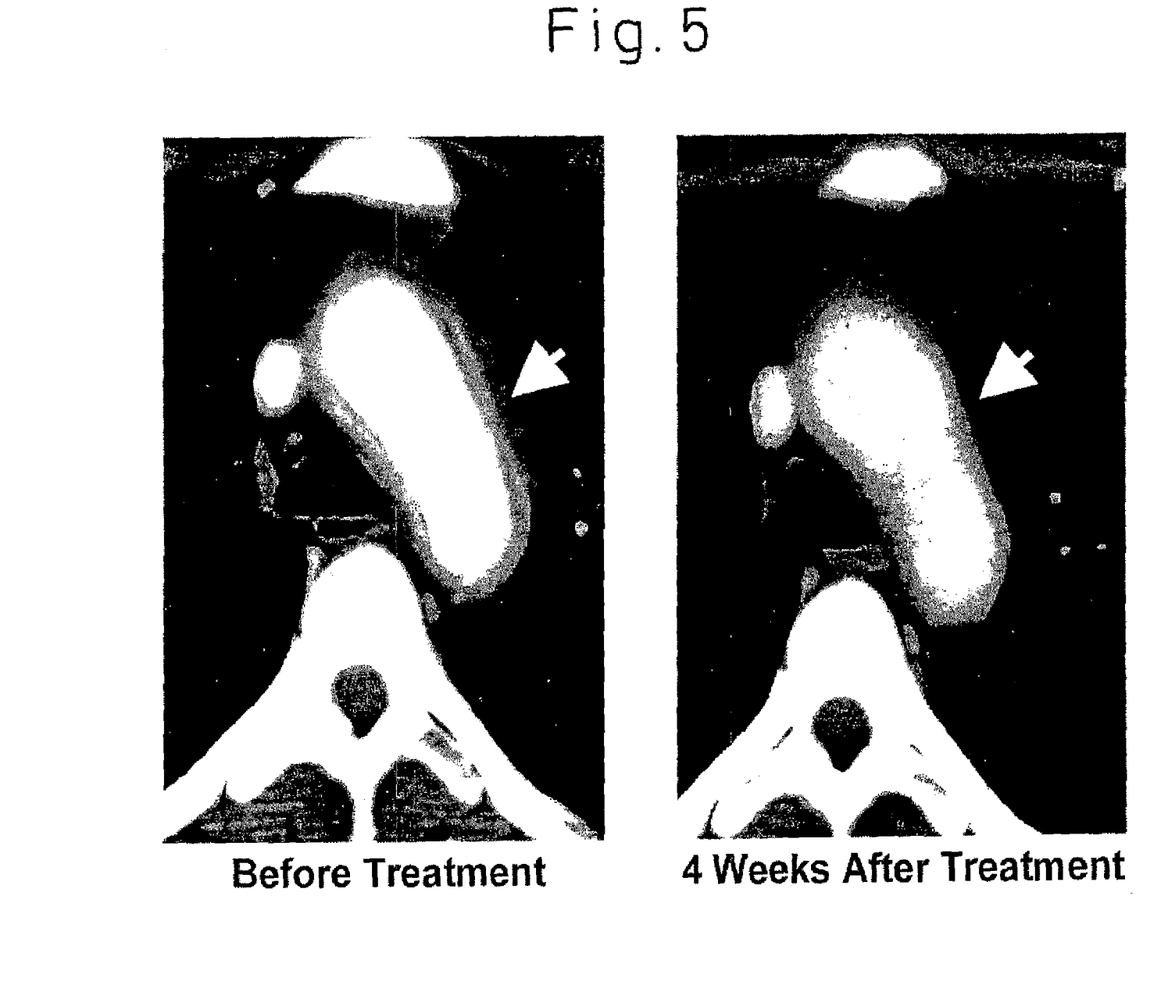
FIG. 5 is a photograph showing the result of CT in the treatment of the vasculitis syndrome with humanized IL-6R antibody, in which the arrow indicates the aortic arch.
Figure 6:
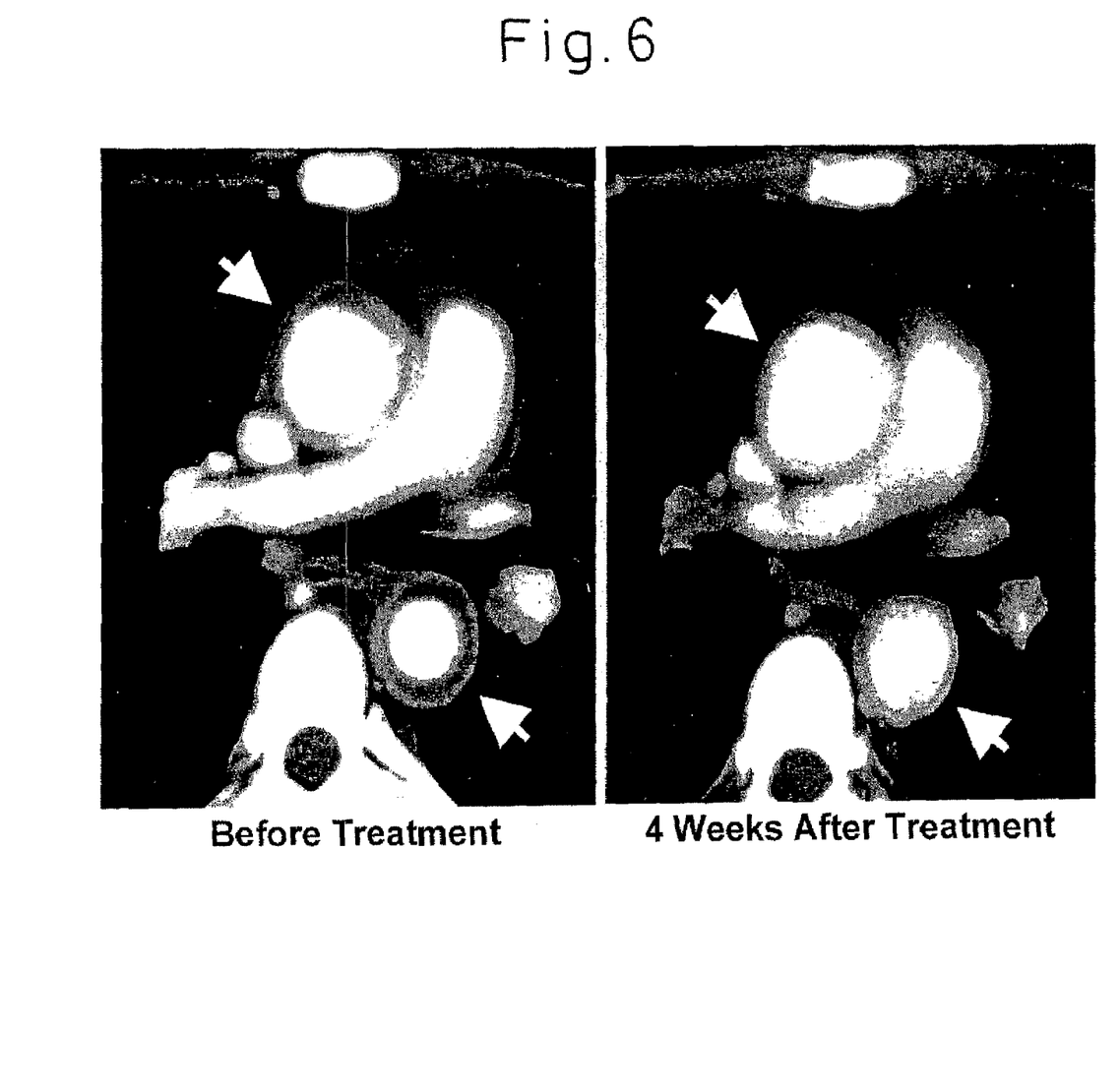
FIG. 6 is a photograph showing the result of CT in the treatment of the vasculitis syndrome with humanized IL-6R antibody, in which the upper arrow indicates the ascending aorta and the lower arrow indicates the descending aorta

As shown in FIGS. 1-6, CT revealed the prominent hypertrophy of the blood vessel wall in the ascending aorta, the aortic arch trifurcation, and the descending aorta. Stenosis was noted in the left subclavian artery (1t. SCA). Severe inflammation was noted with CRP 12.6 mg/dl, and due to a severe persistent chest pain, a reduction in body weight of 5 kg per month, and attacks of unconsciousness occurred, the drip infusion of MRA 200 mg/week was used. About two weeks later, CRP turned negative. One month later, chest pain improved, and as seen in FIGS. 1-6, improvement in the hypertrophy of the blood vessel wall in the ascending aorta, the aortic arch trifurcation and the descending aorta, and enlargement of the lumen of the blood vessels were observed and, furthermore, the blood flow in carotid artery improved. Also fecal hemoglobin turned negative, and symptoms of ulcerative colitis disappeared. During the MRA therapy, blood levels of TNFα increased, but without any aggravation in symptoms. Improvement in the hypertrophy of the aorta wall and enlargement of the lumen of the blood vessels were maintained even at the time of two years after the MRA therapy. Takayasu's arteritis is also termed as the pulseless disease, and in this patient as well the pulse could not be felt, but after treatment the pulsation of arteries of the radius and the cubitus could be felt at the wrist. Due to a prolonged use of MRA, blood levels of IL-6 decreased from 1720 pg/ml to 100 pg/ml.

Case 2:

A 42-year old male. In 1986, arteritis nodosa (the skin type) developed, and despite treatments with PSL, azathiopurine, colchicine and anti-coagulants, remission and aggravation repeated. In 1995 and after, cyclophosphamide was used in combination with the mPSL pulse therapy, but without effect. From 1997, bolus administration of azathiopurine, cyctophosphamide and γ-globulin was started, and from 2000, the cyclophosphamide pulse therapy and leukopheresis were started, but without effect. Skin grafting was performed on the skin ulcer due to vasculitis, but without effect, and, due to aggravation, right fibula removal and B-K amputation were performed. Necrotic vasculitis further aggravated, and the ulcer in the lower limb was enlarging. After starting treatment with a humanized anti-IL-G receptor antibody 200 mg/week, fever and skin erythema and muscle pains that were previously observed improved. Though the removal of the right thigh could not be avoided, leukocyte counts normalized with reduced IL-6 in the blood, and no aggravation in skin ulcer was noted thereafter.

Discussion:

Since MRA was effective for patients with intractable vasculitis that could not be controlled by the conventional treatments, it was suggested that the IL-6 inhibition treatment could provide a novel method of treatment for vasculitis. This means that IL-6 is indispensable for the establishment of pathology of vasculitis. Also, as the reduction of IL-6 per se was noted in all cases, it demonstrated that the IL-6 inhibition treatment not only has an anti-inflammatory effect but acts on the essential nature of vasculitis, Reference Example 1

Preparation of Human Soluble IL-6 receptor

Soluble IL-6 receptor was prepared by the PCR method using a plasmid pBSEF2R.236 containing cDNA that encodes IL-6 receptor obtained according to the method of Yamasaki et al., (Yamasaki, K. et al., Science (1988) 241, 825-828). Plasmid pBSF2R.236 was digested with a restriction enzyme Sph I to obtain the cDNA of IL-6 receptor, which was then inserted into mp18 (manufactured by Amersham). Using a synthetic oligoprimer designed to introduce a stop codon into the cDNA of IL-6 receptor, a mutation was introduced into the cDNA of IL-6 receptor by the PCR method using the in vitro Mutagenesis System (manufactured by Amersham). The procedure resulted in the introduction of a stop codon to the amino acid at position 345, and gave cDNA encoding soluble IL-6 receptor.

In order to express the cDNA of soluble IL-6 receptor in CHO cells, it was ligated to plasmid pSV (manufactured by Pharmacia) to obtain plasmid pSVL344. The cDNA of soluble IL-6 receptor that was cleaved with Hind III-Sal I was inserted to plasmid pECEdhfr containing the cDNA of dhfr to obtain plasmid pECEdhfr344 that can be expressed in the CHO cells.

Ten μg of plasmid pECEdhfr344 was transfected to a dhfr-CHO cell line DXB-11 (Urlaub G. et al., Proc. Natl. Acad. Sci. USA (1980) 77, 4216-4220) by the calcium phosphate precipitation method (Chen C. et al., Mol. Cell. Biol. (1987) 7, 2745-2751). The transfected CHO cells were cultured for 3 weeks in a nucleoside-free α MEM selection medium containing 1 mM glutamine, 10% dialyzed FCS, 100 U/ml penicillin, and 100 μg/ml streptomycin.

The selected CHO cells were screened by the limiting dilution method to obtain a single CHO cell clone. The CHO cell clone was amplified in 20 nM-200 nM methotrexate (MTX) to obtain a CHO cell line 5E27 that produces human soluble IL-6 receptor. The CHO cell line 5E27 was cultured in an Iscov-modified Dulbecco's medium (IMDM, manufactured by Gibco) containing 5% FBS. The culture supernatant was collected and the concentration of soluble IL-6 receptor in the culture supernatant was determined by ELISA. The result confirmed that soluble IL-6 receptor is present in the culture supernatant.

Reference Example 2

Preparation of Human IL-6 Antibody

Ten μg of the recombinant IL-6 (Hirano et al., Immunol. Lett., (1988) 17, 41) was immunized to BALB/c mice together with Freund's complete adjuvant, and this was repeated every week until anti-IL-6 antibody could be detected in the serum. Immune cells were extracted from local lymph node and were then fused with a myeloma cell line P3U1 using polyethylene glycol 1500. Hybridomas were selected according to the method of Oi et al. (Selective Methods in Cellular Immunology, W.H. Freeman and Co., San Francisco, 351, 1980) that employs the HAT medium, and a hybridoma that produces anti-human IL-6 antibody was established.

The hybridoma that produces anti-human IL-6 antibody was subjected to the IL-6 binding assay as follows. Thus, a 96-well microtiter plate made of flexible polyvinyl (manufactured by Dynatech Laboratories, Inc., Alexandria, Va.) was coated with 100 µl of goat anti-mouse Ig (10µ/ml, manufactured by Cooper Biomedical, Inc., Malvern, Pa.) overnight at 4° C. Subsequently, the plate was treated with 100 µl of PBS containing 1% bovine serum albumin (BSA) at room temperature for 2 hours.

After washing in PBS, 100 µl of the hybridoma culture supernatant was added to each well, and then incubated overnight at 4° C. The plate was washed, $^{125}$I-labeled recombinant IL-6 was added to each well to a concentration of 2000 cpm/0.5 ng/well, and then radioactivity of each well after washing was determined by a gamma counter (Beckman Gamma 9000, Beckman Instruments, Fullerton, Calif.). Of 216 hybridoma clones, 32 were positive in the IL-6 binding assay. From these clones, stable MH166.BSF2 was finally obtained. Anti-IL-6 antibody MH166 produced by said hybridoma has a subtype of IgG1 κ.

Then, the IL-6-dependent mouse hybridoma clone MH60.BSF2 was used to examine a neutralizing activity with respect to the growth of the hybridoma by MH166 antibody. MH60.BSF2 cells were dispensed to $1 \times 10^4/200$ µl/well, and samples containing MH166 antibody were added thereto, cultured for 48 hours, 0.5 µCi/well of $^3$H-thymidine (New England Nuclear, Boston, Mass.) was added, and the culturing was continued for further 6 hours. The cells were placed on a glass filter paper and were treated by the automatic harvester (Labo Mash Science Co., Tokyo, Japan). As the control, rabbit anti-IL-6 antibody was used.

As a result, MH166 antibody inhibited, in a dose dependent manner, the incorporation of $^3$H-thymidine of MH60.BSF2 cells induced by IL-6. This revealed that MH166 antibody neutralizes the activity of IL-6.

Reference Example 3

Preparation of Human Anti-IL-6 Receptor Antibody

Anti-IL-6 receptor antibody MT18 prepared by the method of Hirata et al. (Hirata, Y. et al. J. Immunol., (1989) 143, 2900-2906) was bound to CNBr-activated Sepharose 4B (manufactured by Pharmacia Fine Chemicals, Piscataway, N.J.) according to the attached regimen, and IL-6 receptor (Yamasaki, K. et al., Science (1988) 241, 825-828) was purified. A human myeloma cell line U266 was solubilized with 1 mM p-para-aminophenyl methane sulfonyl fluoride hydrochloride (manufactured by Wako Chemicals) (digitonin buffer) containing 1% digitonin (manufactured by Wako Chemicals), 10 mM triethanolamine (pH 7.8) and 0.15 M NaCl and mixed with MT18 antibody bound to Sepharose 4B beads. Then, the beads were washed six times with the digitonin buffer to prepare the partially purified IL-6 receptor to be used for immunization.

BALB/c mice were immunized tour times every ten days with the above partially purified IL-6 receptor obtained from $3 \times 10^9$ U266 cells, and then a hybridoma was prepared using a standard method. The hybridoma culture supernatant from the growth-positive well was tested for its activity of binding to IL-6 receptor according to the method described below. $5 \times 10^7$ U266 cells were labeled with $^{35}$S-methionine (2.5 mCi) and were solubilized with the above digitonin buffer. The solubilized U266 cells were mixed with a 0.04 ml volume of MT18 antibody bound to Sepharose 4B beads, and then were washed six times with the digitonin buffer. $^{35}$S-methionine-labeled IL-6 receptor was eluted with 0.25 ml of the digitonin buffer (pH 3.4) and was neutralized in 0.025 ml of 1 M Tris (pH 7.4)

0.05 ml of the hybridoma culture supernatant was mixed with 0.01 ml of Protein G Sepharose (manufactured by Pharmacia). After washing, Sepharose was incubated with 0.005 ml $^{35}$S-labeled IL-6 receptor solution prepared as described above. The immunoprecipitate was analyzed by SDS-PAGE to investigate the hybridoma culture supernatant that reacts with IL-6 receptor. As a result, the reaction-positive hybridoma clone PM-1 (FERM BP-2998) was established. The antibody produced from the hybridoma PM-1 has a subtype of IgG1κ.

The inhibitory activity of IL-6 binding of the antibody produced by the hybridoma PM-1 to human IL-6 receptor was studied using the human myeloma cell line U266. A human recombinant IL-6 was prepared from *E. coli* (Hirano et al., Immunol. Lett., (1988) 17, 41-45), and was labeled with $^{125}$I using the Bolton-Hunter reagent (New England Nuclear, Boston, Mass.) (Taga, T. et al., J. Exp. Med. (1987) 166, 967-981).

$4 \times 10^5$ U266 cells were cultured with the culture supernatant of 70% (v/v) hybridoma PM-1 together with 14,000 cpm of $^{125}$I-labeled IL-6 for one hour. Seventy µl of the sample was layered on 300 µl FCS in a 400 µl microfuge polyethylene tube. After centrifugation, the radioactivity of the cell was determined.

The result revealed that the antibody produced by the hybridoma PM-1 inhibits the binding of IL-6 to IL-6 receptor.

Reference Example 4

Preparation of Mouse Anti-IL-6 Receptor Antibody

A monoclonal antibody directed against mouse IL-6 receptor was prepared according to the method described in Saito, et al., J. Immunol. (1991) 147, 168-173.

The CHO cells that produce mouse soluble IL-6 receptor were cultured in the IMDM culture liquid containing 10% FCS. From the culture supernatant, mouse soluble IL-6 receptor was purified using an affinity column in which anti-mouse IL-6 receptor antibody RS12 (see Saito, et al., supra) was fixed to Affigel 10 gel (manufactured by Biorad).

The mouse soluble IL-6 receptor (50 µg) thus obtained was mixed with Freund's complete adjuvant, which was then injected to the abdomen of Wistar rats. From 2 weeks after the administration, the animals were boosted with Freund's incomplete adjuvant. On day 45, rat spleen cells were harvested, and about $2 \times 10^8$ cells thereof were fused with $1 \times 10^7$ mouse myeloma cells P3U1 using a 50% PEG1500 (manufactured by Boehringer Mannheim) according to the conventional method, and then were screened by the HAT culture medium.

After the hybridoma culture supernatant was added to the plate coated with rabbit anti-rat IgG antibody (manufactured by Cappel), mouse soluble IL-6 receptor was reacted. Subsequently, using rabbit anti-mouse IL-6 receptor antibody and alkaline phosphatase-labeled sheep anti-rabbit IgG, hybridomas producing antibody directed against mouse soluble IL-6 receptor were screened by ELISA. After antibody production was confirmed, the hybridoma clones were subscreened twice to obtain a single hybridoma clone. The clone was designated as MR16-1.

The neutralizing activity of the antibody produced by the hybridoma on signal transduction of mouse IL-6 was examined by $^3$H-thymidine incorporation using MH60.BSF2 cells (Matsuda, T. et al., J, Immunol. (1988) 18, 951-956). To a 96-well plate, MH60.BSF2 cells were prepared at $1\times10^4$ cells/200 µl/well. To the plate were added 10 pg/ml mouse IL-6 and MR16-1 antibody or RS12 antibody at 12.3-1000 ng/ml, and then were cultured at 37° C. and 5% $CO_2$ for 44 hours, and then 1 µCi/well of $^3$H-thymidine was added. After 4 hours, the incorporation of $^3$H-thymidine was measured. As a result, MR16-1 antibody suppressed the incorporation of $^3$H-thymidine by the MH60.BSF2 cells.

Thus, it was demonstrated that the antibody produced by the hybridoma MR16-1 (FERM BP-5875) inhibits the binding of IL-6 to IL-6 receptor.

The invention claimed is:

1. A method of treating vasculitis comprising administering an antibody against interleukin-6 (IL-6) receptor to a subject in need thereof.

2. The method according to claim 1 wherein said vasculitis is polyarteritis nodosa.

3. The method according to claim 1 wherein said vasculitis is the aortitis syndrome.

4. The method according to claim 1 wherein said antibody against IL-6 receptor is a monoclonal antibody against IL-6 receptor.

5. The method according to claim 1 wherein said antibody against IL-6 receptor is a monoclonal antibody against human IL-6 receptor.

6. The method according to claim 5 wherein said monoclonal antibody against human IL-6 receptor is PM-1 antibody.

7. The method according to claim 1 wherein said antibody against IL-6 receptor is a monoclonal antibody against mouse IL-6 receptor.

8. The method according to claim 7 wherein said monoclonal antibody against mouse IL-6 receptor is MR16-1 antibody.

9. The method according to claim 1 wherein said antibody against IL-6 receptor is a recombinant antibody.

10. The method according to claim 1 wherein said antibody against IL-6 receptor is a chimeric antibody, humanized antibody, or a human antibody against IL-6 receptor.

11. The method according to claim 10 wherein said humanized antibody against IL-6 receptor is a humanized PM-1 antibody.

* * * * *